United States Patent
Yuan et al.

(10) Patent No.: US 10,532,131 B2
(45) Date of Patent: *Jan. 14, 2020

(54) OSTEOINDUCTIVE CALCIUM PHOSPHATES

(71) Applicant: Progentix Orthobiology B.V., Bilthoven (NL)

(72) Inventors: Huipin Yuan, Zeist (NL); Joost Dick de Bruijn, Amersfoort (NL)

(73) Assignee: NuVasive Netherlands B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/792,305

(22) Filed: Jul. 6, 2015

(65) Prior Publication Data

US 2016/0067382 A1    Mar. 10, 2016

Related U.S. Application Data

(63) Continuation of application No. 12/279,533, filed as application No. PCT/NL2007/050069 on Feb. 19, 2007, now abandoned.

(Continued)

(30) Foreign Application Priority Data

Feb. 17, 2006    (EP) ..................................... 06075368

(51) Int. Cl.
*A61L 27/12*    (2006.01)
*A61F 2/28*    (2006.01)

(Continued)

(52) U.S. Cl.
CPC ............... *A61L 27/56* (2013.01); *A61L 27/12* (2013.01); *A61L 27/3847* (2013.01); *A61L 27/54* (2013.01); *A61L 27/58* (2013.01); *A61F 2/28* (2013.01); *A61F 2002/2835* (2013.01); *A61F 2310/00293* (2013.01);
(Continued)

(58) Field of Classification Search
None
See application file for complete search history.

(56) References Cited

U.S. PATENT DOCUMENTS 4,294,753 A * 10/1981 Urist ..................... A61L 27/227
424/549
4,497,075 A * 2/1985 Niwa ..................... A61K 33/42
106/462

(Continued)

FOREIGN PATENT DOCUMENTS

EP    0267624    5/1988
JP    04212369 A *    8/1992
(Continued)

OTHER PUBLICATIONS

Habibovic et al., Biomaterials (2005) 26(17):3565-3575.
(Continued)

*Primary Examiner* — Megan Y Wolf

(57) ABSTRACT

The invention relates to a porous osteoinductive calcium phosphate material having an average grain size in a range of 0.1-1.50 µm, having a porosity consisting essentially only of micropores in a size range of 0.1-1.50 µm, and having a surface area percentage of micropores in a range of 10-40%.

11 Claims, 12 Drawing Sheets

Related U.S. Application Data

(60) Provisional application No. 60/774,840, filed on Feb. 17, 2006.

(51) Int. Cl.

| | | |
|---|---|---|
| *A61L 27/56* | (2006.01) | |
| *A61L 27/38* | (2006.01) | |
| *A61L 27/54* | (2006.01) | |
| *A61L 27/58* | (2006.01) | |

(52) U.S. Cl.
CPC ... *A61L 2300/412* (2013.01); *A61L 2300/414* (2013.01); *A61L 2300/45* (2013.01); *A61L 2300/64* (2013.01); *A61L 2430/02* (2013.01)

(56) References Cited

U.S. PATENT DOCUMENTS

| | | | |
|---|---|---|---|
| 4,693,986 A | 9/1987 | Vit et al. | |
| 5,017,518 A * | 5/1991 | Hirayama | A61L 27/12 |
| | | | 106/35 |
| 5,064,436 A * | 11/1991 | Ogiso | A61L 27/12 |
| | | | 623/23.56 |
| 6,511,510 B1 * | 1/2003 | de Bruijn | A61L 27/12 |
| | | | 623/23.51 |
| 7,942,934 B2 * | 5/2011 | Yuan | A61L 27/12 |
| | | | 424/602 |
| 2001/0021389 A1 * | 9/2001 | Starling | B01J 20/28019 |
| | | | 424/422 |
| 2002/0098222 A1 * | 7/2002 | Wironen | A61F 2/28 |
| | | | 424/423 |
| 2004/0029699 A1 * | 2/2004 | Lemaitre | A61L 27/12 |
| | | | 501/1 |
| 2005/0191226 A1 | 9/2005 | Tuan et al. | |
| 2006/0257492 A1 * | 11/2006 | Wen | A61K 33/42 |
| | | | 424/489 |
| 2006/0292200 A1 | 12/2006 | Delaney | |

FOREIGN PATENT DOCUMENTS

| | | |
|---|---|---|
| JP | 4212369 | 1/2009 |
| WO | 1999034844 | 7/1999 |
| WO | 2006115398 | 11/2006 |

OTHER PUBLICATIONS

International Search Report for PCT/NL2007/050069, dated May 31, 2007, 3 paQes.

Yamasaki et al., Biomaterials (1992) 13(5):308-312.

* cited by examiner

OSTEOINDUCTIVE CALCIUM PHOSPHATES

CROSS-REFERENCE TO RELATED APPLICATIONS

This patent application is a Continuation of U.S. patent application Ser. No. 12/279,533, filed Apr. 21, 2010 (abandoned), which is a National Stage Entry of International Patent App. No. PCT/NL2007/050069, filed Feb. 19, 2007, which claims the priority of U.S. Provisional Application Ser. No. 60/774,840 filed on Feb. 17, 2006. The foregoing related applications are incorporated herein by reference in their entireties.

FIELD OF THE INVENTION

The invention relates to an osteoinductive material, to a method for preparing said material and to a material produced that way.

BACKGROUND OF THE INVENTION

Autologous bone harvested from the patient's own bone is the gold standard bone substitute for repairing large bone defects. However, the amount of autologous bone harvestable from a patient is limited and the bone subtraction itself poses significant health risks and results in loss of structural integrity of the remaining bone.

Developments in tissue engineering have provided synthetic implants, for instance in the form of scaffold materials, which allow attachment of bone cells and ingrowth of new bone tissue and subsequent deposition of new bone mineral. The synthetic materials may either be grafted ex vivo with bone cells prior to implantation or may be implanted as naked scaffolds that attract bone cells from the periphery to the site of the implant.

Recent advances in tissue engineering have produced a variety of valuable scaffold materials. Calcium phosphates such as hydroxyapatite (HA; the mineral phase of bone), biphasic calcium phosphate (BCP) and α- or β-tricalcium phosphate (TCP) are known to possess both osteoconductive (bioactive) as well as osteoinductive properties and provide very suitable scaffold materials. The bioactive nature of calcium phosphates allows them to function as a template for new bone formation by osteogenic cells through deposition of new mineral material at the scaffold's surface and is an important feature of the scaffold material. The osteoinductive nature of calcium phosphates is a qualitative feature, i.e. the capacity to induce the development of the new bone tissue, thereby enhancing the rate of deposition of new mineral depends on various material parameters. Bone induction is generally defined as the mechanism by which a mesenchymal tissue is induced to change its cellular structure to become osteogenic.

In general, porous calcium phosphates have been found to exhibit osteoinductivity. For instance, Yamasaki et al., in Biomaterials 13:308-312 (1992), describe the occurrence of heterotopic ossification (formation of new bone in tissue that do not normally ossify) around porous hydroxyapatite ceramic granules, but not around dense granules. The porous granules range in size from 200 to 600 µm, and have a continuous and interconnected microporosity of which the pores range in diameter from 2 to 10 µm.

U.S. Pat. No. 6,511,510 describes a biocompatible and biodegradable calcium phosphate that exhibits improved osteoinductivity over the porous hydroxyapatite granules of Yamasaki et al. The biodegradable calcium phosphate has a total porosity of 20 to 90%, and encompasses both macropores ranging in size from 0.1 to 1.5 mm, as well as micropores ranging in size from 0.05 to 20 µm. The biodegradable calcium phosphate material is produced by mould casting and blocks can subsequently be granulated or cut to smaller size particles. The material, when implanted, is suitable to function as a (temporary) substitute for bone.

Despite the availability of the above materials, it would be advantageous if biomaterials for use in connection with living tissues could be provided with even better osteoinductive properties, i.e. that result in even faster and more profound bone formation. It would also be advantageous if such osteoinductive materials could be easily introduced in the body of the mammal, most preferably such that they provide an easily implantable and effective scaffold material for the production of new bone in both osseous and non-osseous sites. Such material would be of much use for the production of de novo autologous bone, which might subsequently be used as bone substitute for repairing large bone defects.

SUMMARY OF THE INVENTION

The present invention provides a calcium phosphate material having excellent osteoinductive properties.

In a first aspect the present invention provides a porous osteoinductive calcium phosphate material having an average grain size in a range of 0.1-1.50 µm, a porosity comprising micropores in a size range of 0.1-1.50 µm, and having a surface area percentage of micropores in a range of 10-40%.

In a preferred embodiment, the surface area percentage of micropores is below 40%, most preferably in a range from 10-25%.

A porous calcium phosphate of the invention preferably has a protein adsorption capacity, expressed as the percentage of protein absorbed by a volume of 1 ml of said calcium phosphate from a volume of 3 ml of a 1% aqueous solution of fetal bovine serum (FBS) in the presence of 25 ppm sodium azide (NaN$_3$) after 24 hrs at 37° C., of at least 40%.

In a preferred embodiment the porosity of the porous calcium phosphate material consists essentially only of micropores in the specified size range, and is free of macropores.

A porous calcium phosphate of the invention is preferably in the form of microparticles having a particle size ranging from about 50 to about 1500 µm, more preferably from about 200 to about 300 µm, most preferably 212-300 µm.

The material of the invention shows excellent osteoinductive behaviour in living tissue. The formation of bone tissue at the surface of the material of the invention assists in a favourable acceptation of an implant made of said material. Moreover, the formation of the bone tissue accelerates the recovery of any damage in the bone structure, which forms the reason for applying the implant.

An advantage of the material of the present invention in the form of microparticles is that it has excellent flowing properties. The sand-like constitution of the microparticulate material allows it to be injected without an additional fluidic carrier. Thus, the material in such an embodiment may be used as an injectable, although it may also be used in admixture with for instance a liquid carrier.

In a preferred embodiment, the calcium phosphate of the invention is a calcium phosphate selected from the group consisting of octacalcium phosphate, apatites, such as hydroxyapatite and carbonate apatite, whitlockites, such as β-tricalcium phosphate and α-tricalcium phosphate, and combinations thereof. More preferably the calcium phosphate is resorbable biphasic calcium phosphate (BCP) and resorbable tricalcium phosphate, most preferably β-tricalcium phosphate.

In another aspect, the present invention relates to the porous calcium phosphate of the invention for use as a medical implant material or tissue scaffold.

It has been found that a material of the invention has osteoinductive properties that are improved over the materials of the prior art. It is a feature of the material that it exhibits microporosity (pores <5 µm), preferably interconnected microporosity. In a preferred embodiment, the material is essentially free of macropores (pores ranging in size from 0.1 to 1.5 mm).

A porous calcium phosphate of the invention may suitably be used for inducing the formation of bone tissue in a living organism, as an implant material alone or combined with growth factors or/and cells for the production of autologous bone in a non-osseous site or for the production of a medical implant or device alone or combined with growth factors or/and cells.

A porous calcium phosphate of the invention may suitably be used in dental surgery.

In another aspect, the present invention provides a method for producing a porous osteoinductive calcium phosphate ceramic, comprising providing an aqueous slurry of a calcium phosphate powder having a particle size of 1.0-8.0 µm, preferably of 2.0-4.0 µm, a foaming agent and optionally a porogenic agent in water; subjecting the slurry to conditions which cause foaming of said slurry; drying the resultant foamed slurry, optionally removing the porogenic agent, to provide a porous green body and sintering the porous green body at a temperature between 1050° C. and 1150° C. to provide the porous sintered calcium phosphate; and optionally milling the sintered calcium phosphate to particles and collecting the particles having a particle size ranging from about 50 to about 1500 µm.

In a preferred embodiment, the method further includes the step of milling the sintered calcium phosphate to particles, wherein the particles are collected by using sieves, most preferably 212 and 300 µm sieves to provide a microparticle fraction of 212-300 µm.

In a preferred embodiment of a method of the invention the calcium phosphate powder is a powder that is composed of crystals having a crystal size between 0.01 and 1 µm, preferably between 0.05 and 0.5 µm.

In another preferred embodiment of a method of the invention the foaming agent is hydrogen peroxide.

In yet another preferred embodiment of a method of the invention the porogenic agent comprises of naphthalene particles, and wherein the porogenic agent is removed by evaporation at 80-110° C.

In still another preferred embodiment of a method of the invention said conditions which cause foaming of said slurry comprise heating of the slurry to about 50-70° C.

In another preferred embodiment of a method of the invention the dried and foamed slurry is sintered at a temperature of 1050-1100° C. in the case of TCP, more preferably 1050-1075° C., or at a temperature of 1100-1150° C. in case of HA and/or BCP.

In another preferred embodiment of a method of the invention the calcium phosphate powder is TCP or BCP powder.

In yet another preferred embodiment of a method of the invention the microparticles collected after milling of the sintered calcium phosphate are subsequently cleaned ultrasonically with acetone, ethanol and/or water, and optionally dried and sterilized.

In yet a further preferred embodiment of a method of the invention the calcium phosphate powder is an oven dried milled powder having particles of irregular shape.

In another aspect, the present invention relates to a porous osteoinductive calcium phosphate obtainable by a method of the invention.

BRIEF DESCRIPTION OF THE DRAWINGS

FIG. 1 show the XRD pattern of the material described in Example 1.

FIG. 2 is a morphological view (SEM image) of micropores in the material described in Example 1.

FIG. 3 presents a plot of incremental pore volume versus average micropore diameter as determined by mercury intrusion (indicating that incremental pore volume peaks at pore size of 1.1 µm) as described in Example 1.

DETAILED DESCRIPTION OF THE INVENTION

Figure 1:
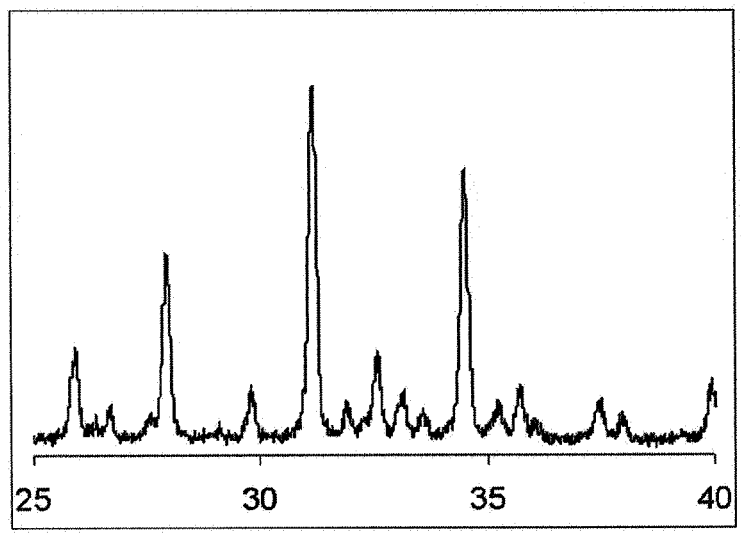
FIGS. 1-3 show the physicochemical properties of an osteoinductive granular tricalcium phosphate ceramic material according to the invention as described in more detail in Example 1.

The term "particle" is used herein to indicate a granular or powdery material (terminology depending on the absolute size of the particles). A microparticle is a particle having a size less than 1 mm (i.e. several to several hundred micrometers).

The material of the present invention has essentially an open porous structure, wherein the individual pores are interconnected by openings or voids. The structure of calcium phosphate matrix itself is upon microscopic observation not smooth but grainy, wherein the structural material is structurally organised in the form of packed grains spaced by pores. The term "grain" is used to indicate the individually recognizable "particles" that form the continuous matrix of the porous calcium phosphate, i.e. the crystals as embedded in the ceramic material that are structurally connected to other grains, as visible in SEM micrographs. The terms "grain" and "crystal" can be used interchangeably herein, whereas the term "grain" better indicates the globular nature of the smallest individually recognizable structural "elements" in the matrix. The term "grain" is thus not related to a granular or particulate form of the material, but indicates an internal structure.

The term "particles having irregular shapes" means that the particles of a calcium phosphate powder (which may itself also have a grainy structure) are not spherical.

The term "micropore" is used in its art-recognized form and indicates a pore in a porous material having a size less than 50 µm, preferably less than 10 µm, more preferably less than 1.5 µm. The average (or mean) diameter of at least 10 of the largest micropores as visible in SEM micrographs is determined for determining the size of the micropores in the porous calcium phosphate);

The term "surface area percentage of micropores" indicates the surface area of a sectional view of the porous calcium phosphate associated with micropores as a percentage of the total surface area associated with both micropores and dense material.

The term "protein adsorption" indicates the amount of protein absorbed by a volume of 1 ml of the porous calcium phosphate when soaked in 3 ml of a 1% fetal bovine serum (FBS) aqueous solution containing 25 ppm NaN$_3$ after incubation at 37° C. for 24 hrs, whereby the amount absorbed is 100% minus the percentage remaining in solution and of which the protein content is determined before and after contact with the calcium phosphate.

A porous calcium phosphate material in aspects of the present invention may be based on any calcium phosphate (CaP), such as a CaP obtained by precipitation from an aqueous solution at low temperature or by a high temperature (thermal) process. Highly preferred calcium phosphates are the calcium orthophosphates. The term "calcium orthophosphate" as used herein refers to a family of compounds, each of which contains a calcium cation, Ca$^{2+}$, and a phosphate anion, PO$_4^{3-}$. Under this definition, there are multiple calcium orthophosphates, including monocalcium orthophosphate (monobasic), dicalcium orthophosphate (dibasic), tricalcium orthophosphate (tribasic), and hydroxyapatite (penta calcium triphosphate).

Although this invention is described mainly in terms of calcium orthophosphate, other suitable materials useful herein include for instance calcium pyrophosphates (e.g., dicalcium diphosphate (Ca$_2$P$_2$O$_7$, synonym: calcium pyrophosphate), calcium pyrophosphate dihydrate (CPPD, Ca$_2$P$_2$O$_7$.2H$_2$O), and calcium dihydrogen diphosphate (CaH$_2$P$_2$O$_7$; synonyms; acid calcium pyrophosphate, monocalcium dihydrogen pyrophosphate)), and polyphosphate ((CaP$_2$O$_6$)$_n$, n≥2; synonyms: calcium metaphosphates, calcium polymetaphosphates), and combinations of the various phosphates.

Non-limiting examples of the calcium phosphate compound that may be used in aspects of the invention are:

α-tricalcium phosphate (α-TCP, α-Ca$_3$(PO$_4$)$_2$, synonyms: whitlockite, tricalcium phosphate, calcium phosphate tribasic), either anhydrous or as hydrate;

β-tricalcium phosphate (β-TCP, β-Ca$_3$(PO$_4$)$_2$, synonyms: whitlockite, tricalcium phosphate, calcium phosphate tribasic), either anhydrous or as hydrate;

amorphous calcium phosphate (ACP, Ca$_3$(PO$_4$)$_2$.nH$_2$O, n=3-4.5, Ca/P ratio=1.5)

apatite (calcium fluoro-phosphate, Ca$_5$(F,Cl,OH)(PO$_4$)$_3$)

calcium dihydrogen phosphate (Ca(H$_2$PO$_4$)$_2$);

calcium dihydrogen phosphate hydrate (Ca(H$_2$PO$_4$)$_2$.H$_2$O)

calcium hydrogen phosphate hydrate (CaHPO$_4$.2H$_2$O);

calcium hydrogen phosphate, anhydrous (CaHPO$_4$), calcium-deficient hydroxyapatite or precipitated hydroxyapatite (PHA) Ca$_{10-x}$(HPO$_4$)$_x$(PO$_4$)$_{6-x}$(OH)$_{2-x}$ (0≤x≤1) with Ca/P ratio varying from 1.5 to 1.67 carbonate apatite (Ca$_5$(PO$_4$, CO$_3$)$_3$F)

dicalcium phosphate anhydrous (DCPA, CaHPO$_4$)

dicalcium phosphate dihydrate (DCPD, CaHPO$_4$.2H$_2$O);

fluoroapatite (FA, Ca$_5$(PO$_4$)$_3$F);

hydroxyapatite (HA, Ca$_5$(PO$_4$)$_3$OH, synonyms: (penta) calcium triphosphate);

monocalcium phosphate anhydrous (MCPA, Ca(H$_2$PO$_4$)$_2$);

monocalcium phosphate monohydrate (MCPM, Ca(H$_2$PO$_4$)$_2$.H$_2$O);

octacalcium phosphate (OCP, Ca$_8$H$_2$(PO$_4$)$_6$.5H$_2$O);

oxyapatite (Ca$_{10}$(PO$_4$)$_6$O);

tetracalcium phosphate (TTCP, Ca$_4$(PO$_4$)$_2$O);

mixtures of two or more of the above such as mixtures of MCPM or MCPA with another CaP such as α-tricalcium phosphate or β-tricalcium phosphate, and composites of two or more of the above such as composites of β-TCP and hydroxyapatite (Ca/P-1.67), e.g. biphasic calcium phosphate (BCP).

The calcium phosphates, particularly in case they are derived from natural sources, may be calcined prior to use. As the osteoinductive material of the invention is preferably used as an implant in living tissue, the calcium phosphate is preferably synthetic. Moreover, the osteoinductive material is preferably both sufficiently compatible and sufficiently biodegradable for use as an implant in living tissue. Thus, the calcium phosphate on which the osteoinductive material is based is preferably (bio)resorbable, meaning that it exhibits chemical dissolution and cell-mediated resorption when placed in a mammalian body.

An osteoinductive material according to the invention is preferably based on HA, α-TCP, β-TCP, octacalcium phosphate, or combinations thereof, such as BCP. An osteoinductive material according to the invention is most preferably based on a BCP or TCP.

The material of the present invention is porous. The porosity of the material may comprise both macropores and micropores, but preferably consists essentially of micropores in a size range of 0.1-3.0 μm, preferably of 0.1-2 μm, more preferably of 0.1-1.5 μm, still more preferably from 0.5-1.5 μm. The total porosity ranges from 20 to 90%, preferably from 40 to 70%.

The invention further relates to a process for preparing an osteoinductive material as described above and to an osteoinductive material obtainable by said method.

A method of the invention for producing an osteoinductive material based on calcium phosphate, comprises the steps of providing an aqueous slurry of a calcium phosphate powder, a foaming agent and optionally a porogenic agent in water; subjecting the slurry to conditions which cause foaming of said slurry; drying the resultant foamed slurry and optionally removing the porogenic agent, and sintering the dried and foamed slurry to obtain a porous sintered calcium phosphate ceramic. The method may optionally be followed by the steps of milling the sintered calcium phosphate ceramic to particles and collecting the particles having a desirable particle size.

The preparation of a green body suitably comprises the formation of a slurry of a calcium phosphate (CaP), wherein said CaP is preferably in the form of a powder, suspended in a solution containing a foaming agent. The concentration of the foaming agent (e.g. $H_2O_2$) in the foaming agent solution is suitably in the range from 0.1% to 10.0% and the solvent is suitably water. The ratio wherein foaming agent solution (e.g. $H_2O_2$, 0.1-10.0% in water) and calcium phosphate are mixed to form the slurry is suitably between 10 and 300 ml of foaming agent solution per 100 g of CaP. The amount of porogenic agent (e.g. naphthalene particles, <1400 um) used per 100 g of CaP is suitably between 0-150 g. The slurry may then be foamed (e.g. when using $H_2O_2$ it may be at 50-70° C.) and then dried at for instance 80-110° C. to form the porous green bodies, which are then sintered, and optionally milled to form the microparticles of the present invention.

In order to prepare the present osteoinductive material, a calcium phosphate based material is sintered under such conditions, that an osteoinductive material as described above is obtained.

Preferably the calcium phosphates of the present invention are formed by a process involving sintering of the porous green body at a temperature between 800 and 1300° C., optionally under pressure. The properties of the final product can be adjusted by selecting specific combinations of temperature, pressure and calcium phosphate starting materials. For example, pure HA may be formed by using an apatite with a Ca/P ratio of 1.67, whereas TCP may be formed by using an apatite with a Ca/P ratio of 1.5. When for instance apatites with varying Ca/P ratios are sintered, different amounts of HA and TCP are formed in the final ceramic, resulting in biphasic calcium phosphates (BCPs). Another factor that is determined by the sintering parameters is the residual microporosity. The microporosity of the ceramics may in some embodiments of a method for their production be due to gaps left between the sintered particles, which—in turn—is influenced by the crystallization of the CaP used.

In accordance with a preferred embodiment of the invention, the porous calcium phosphate ceramic is made up of crystals (i.e. grains). Preferably, the size of the crystals is similar to the size of the micropores. Thus, the size of the crystals lies preferably between 0.1 and 3 μm, more preferably between 0.1 and 2 μm, still more preferably between 0.1 and 1.5 μm, and even more preferably between 0.5 and 1.5 μm.

Dense and porous calcium phosphates ceramics are generally produced by different sintering techniques. Dense ceramics are produced by compaction under high pressure, resulting in a frequently called "green" state, and are sintered after the compaction process. Porous calcium phosphates of the invention may for instance be produced by using appropriate-sized naphthalene particles as porogenic agent, incorporated in the aqueous slurry of the calcium phosphate starting material. After compaction under high pressure, removal of naphthalene is accomplished by sublimation, which leaves a porous green state. The integrity of this porous green state is maintained through the sintering step. The use of naphthalene particles is for instance described in Moore et al. (2001) *Australian and New Zealand Journal of Surgery* 71:354-361 and Li et al. (2003) *Journal of the American Ceramic Society* 86:65-72.

Another method of producing porous ceramics may for instance rely on the decomposition of hydrogen peroxide to generate a pore-filled structure. In such cases, the hydrogen peroxide functions as a foaming agent, whereby the escaping gas produces the voids that eventually form the pores. The skilled person will understand that also other foaming agents may be used to produce a porous green body, which, upon drying, may be sintered to produce a calcium phosphate based material having the required porosity. The concentrations of the calcium phosphate in the slurry is preferably such that no additional stabilisers or thickeners are required.

A method for preparing a porous calcium phosphate ceramic of the invention based on TCP can be described as follows (the skilled person will understand that a similar procedure is followed for other calcium phosphate starting materials): A TCP powder (irregular shaped TCP powder having a particle size of 2.82 μm at D(v.0.5)) is mixed with an aqueous $H_2O_2$ solution (0.1-5.0 wt %; usually 2 wt %) and naphthalene particles (commercially purchased particles from Sigma Aldrich Chemicals may be sieved through mesh size 1400 μm, the fraction <1400 μm is suitably used) to obtain a slurry of 100 g of TCP powder in 100-250 ml of $H_2O_2$ solution. After that, the slurry is foamed by placing the slurry in an oven without stirring at a temperature of 50-70° C., usually overnight. Then, the foamed slurry is dried in an oven at a temperature between 80-110° C. to obtain the porous green body. The porous green body is then sintered at a temperature of about 1050 to 1100° C. The sintered material is thereafter suitably milled to provide ceramic particles, and a suitable fraction of 212-300 μm (ceramic microparticles) or 1-3 mm (ceramic particles) may then be collected using sieves. The ceramic particles may thereafter be cleaned and sterilized for use. It should be understood that the sintered porous calcium phosphate can also be used unmilled, in particular the slurry may be casted in a mould, dried, sintered and used directly as a scaffold.

As explained above, the size of the pores may be controlled by the particle size of the calcium phosphate powder of the starting material, by the type and amount of foaming agent, by the conditions to which a slurry of the starting material is subjected for obtaining the foamed "green body", by the type, particle size and amount of the optional porogenic agent, and by the sintering temperature. Preferably, the sintering is carried out at a temperature between 800° C. and 1250° C., most preferably between 1050° C. and 1150° C. The duration of the sintering step may suitably be chosen between 1 and 10 hours, preferably between 7 and 9 hours.

Upon sintering, the material is optionally treated with an aqueous solution of an organic acid and washed. The washing may suitably be performed using acetone, ethanol, water or a combination thereof.

An important aspect of the invention is the physical structure of the osteoinductive material. In highly preferred embodiments, the material is in the form of microparticles or granules, i.e. it is preferably a granular, loose material consisting of particles in a size range of 50-1500 μm, preferably 100-500 μm, more preferably 200-300 μm, and most preferably 212-300 μm in particle size. Therefore, after the sintering, the material is preferably ground, for instance in a ball mill, to produce a relatively coarse powder that comprises microparticles in a size range of 50-1500 μm, preferably 100-500 μm, more preferably 200-300 μm, and most preferably 212-300 μm in particle size. Specific size ranges may be retrieved by using sieves, for instance 212 and 300 μm sieves.

Finally, it is preferred to subject the obtained microparticles of the osteoinductive material to a sterilisation treatment, such as a steam, ethylenoxid or gamma sterilisation.

The material of the present invention, particularly in granular form, may be used in the form of an injectable, either alone in the form of a "powder" or in combination with a liquid carrier in the form of a paste.

The material of the present invention may for instance be used as calcium phosphate cement or it may be used for inducing the formation of bone tissue in a living organism.

The material of the present invention may suitably be used as an implant material, i.e. as a scaffold, for the production of autologous bone in a non-osseous site. This ability is due to the highly osteoinductive properties of the material.

The material of the invention may thus be used as a medical implant or medical device formed of a calcium phosphate. It is also possible that the material is used in combination with a medical implant of a different material, such as a metal or a polymeric material, on which the osteoinductive material according to the invention is present in the form of a coating.

It should be noted that the various uses of the material of the present invention include general surgical applications in bone repair, as well as applications in dental surgery.

The invention will now be illustrated by way of the following non-limiting examples. These Examples describe methods to improve bone forming ability of calcium phosphate ceramics (i.e. sintered calcium phosphates, wherein the calcium phosphates may be form any material as described herein, preferably HA, BCP and/or TCP). The improved calcium phosphate ceramics have grain sizes less than 1.50 μm (e.g. in a range of 0.10-1.50 μm), sizes of micropores on their surface smaller than 1.50 μm (e.g. in a range of 0.10-1.50 μm) and an area percentage of the micropores on their surface between 10% and 40%. The preferred grain size of the crystals, size of micropores and area percentage of micropores result in high concentration of protein adsorption onto the ceramics and high bone forming ability (inductive bone formation in non-osseous sites). The improved calcium phosphate ceramics have shown to adsorb protein to its surface in an amount of equivalent to more than 40% protein (40-80%) from 3 ml 1% fetal bovine serum solution into 1.0 ml (or approximately 400 mg) porous ceramic particles (having total porosity of 80%) in 24 hrs. An improved calcium phosphate ceramic of the invention is preferably prepared by a process using oven dried milled calcium phosphate powders having irregular shapes and having particle sizes (diameters) preferably below 8.0 μm D(v.0.5) (e.g. 2.00-4.00 μm). Such materials are preferred over the use of spray dried calcium phosphate powders having regular spherical particles larger than 8.0 μm D(v.0.5). In methods for producing the calcium phosphate ceramics of the invention methods using foaming agents (such as $H_2O_2$) are preferred over other methods such as Isostatic Pressing. In addition, sintering temperatures are preferably between 1050 and 1150° C. For individual calcium phosphates, sintering temperatures may be further optimized. A preferred sintering temperature for TCP is, for instance, a temperature of 1050-1100° C., while a preferred sintering temperature for HA and BCP is 1100-1150° C.

Figure 6:
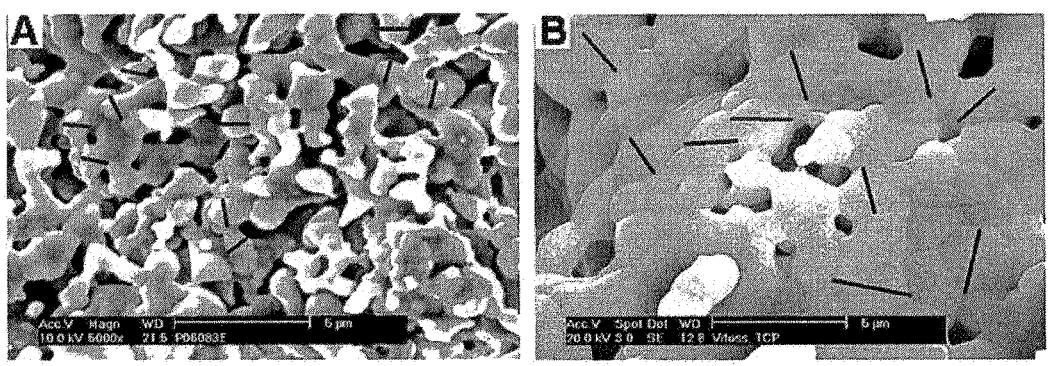
FIG. 6 shows SEM images indicating grain sizes of TCP-01 (A) and TCP-02 (B) described in Example 2.
Figure 7:
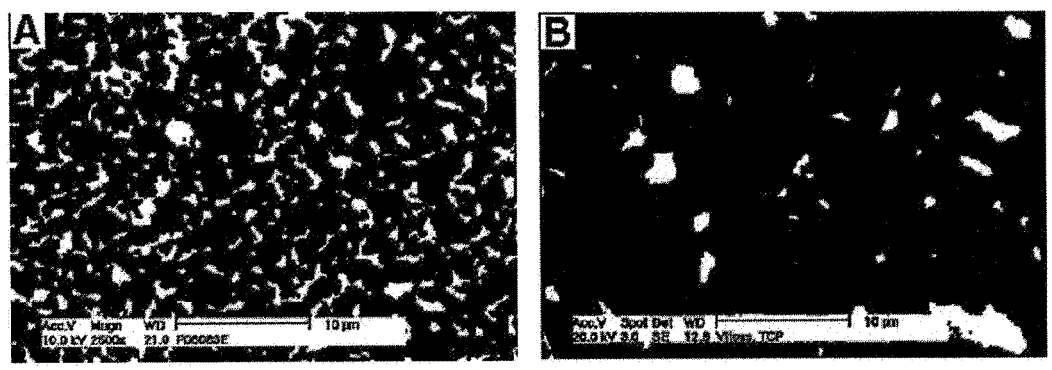
FIG. 7 shows photomicrographs indicating the micropore sizes of TCP-01 (A) and TCP-02 (B) described in Example 2 (Black: TCP grains; white: micropores).

Characteristics and properties of a porous calcium phosphate ceramic that are of importance to its osteoinductive properties are:

grain size (the mean diameter of at least 10 of the largest individually recognizable "particles" that form the continuous matrix, i.e. grains as embedded in the ceramic material and structurally connected therein to other grains, as visible in SEM micrographs, such as for instance indicated in FIG. 6, upon magnification and inspection of a micrograph of the surface of the material representing an area of approximately 10-20 μm×5-15 μm);

micropore size (the mean diameter of at least 10 of the largest micropores as visible in SEM micrographs, such as for instance indicated in FIG. 7, upon magnification and inspection of a surface area of the material of approximately 10-20 μm×5-15 μm);

area percentage of micropores (e.g. the number of pixels in a digital image associated with micropores as a percentage of the total number of pixels of the selected surface area: the area percentage of micropores in sectional view of the material); and protein adsorption (e.g the amount of protein absorbed by a volume of 1 ml of porous ceramic when soaked in 3 ml of a 1% fetal bovine serum (FBS) solution in 25 ppm $NaN_3$ after incubation at 37° C. for 24 hrs, and determining the amount absorbed from the amount remaining in solution, using for instance a BCA™ Protein Assay Kit (Pierce Biotechnology Inc., Rockford, Ill., USA).

Materials exhibiting higher bone forming ability have a smaller grain size, a higher area percentage of micropores and a higher of protein adsorption. TCP-01 of Example 2 is an example of such an improved calcium phosphate ceramic. In general, a calcium phosphate ceramic showing much improved osteoinductive properties has a grain size smaller than 1.50 μm (between 0.10-1.50 μm), a micropore size smaller than 1.50 μm (between 0.10-1.50 μm), area percentage of micropores on calcium phosphate ceramic surface higher than 10% (between 10-40%) and higher protein adsorption which is equivalent to more than 40% protein (between 40-80%) from 3 ml 1% fetal bovine serum solution into 1.0 ml (or approximately 400 mg) porous ceramic particles (having total porosity of 80%) in 24 hrs.

EXAMPLES

Example 1 TCP Microparticles Having a Size of 212-300 μm and Pore Sizes of 0.5-1.5 μm

1.1. Preparation of the Materials

Tricalcium Phosphate Ceramic.

TCP powder (Plasma Biotal, UK) was mixed with $H_2O_2$ solution (1.0-2.0% in water, 100-200 ml/100 g TCP powder) and naphthalene particles (500-1400 μm, 0-150 g/100 g powder), and foamed at 50-70° C. to get porous green bodies. After dried and naphthalene was evaporated at 80-110° C., the green bodies were sintered at 1100° C. for 8 hours. Ceramic particles (1.0-3.0 mm) and microparticles (212-300 μm) were made and cleaned ultrasonically with acetone, ethanol and water, and finally dried at 80° C.

1.2. Characterization of the Materials

The chemistry of the material was analyzed with XRD, micropores were analyzed with SEM (morphology) and Mercury intrusion (micropore size).

Figure 2:
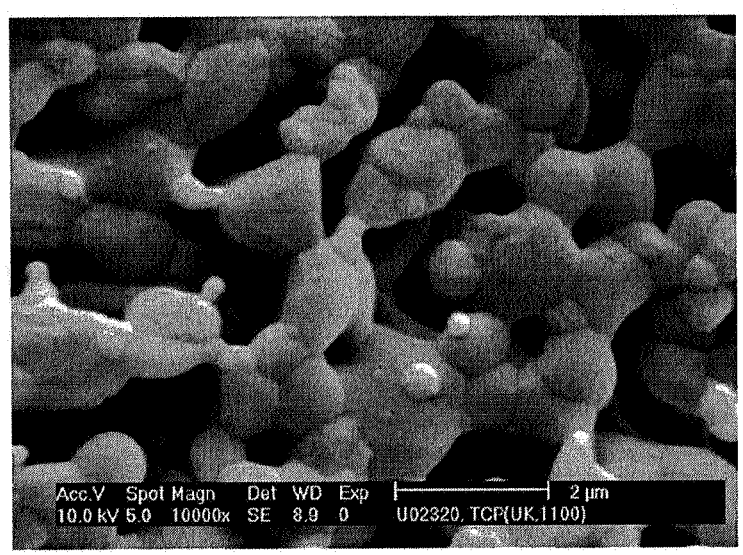
Figure 3:
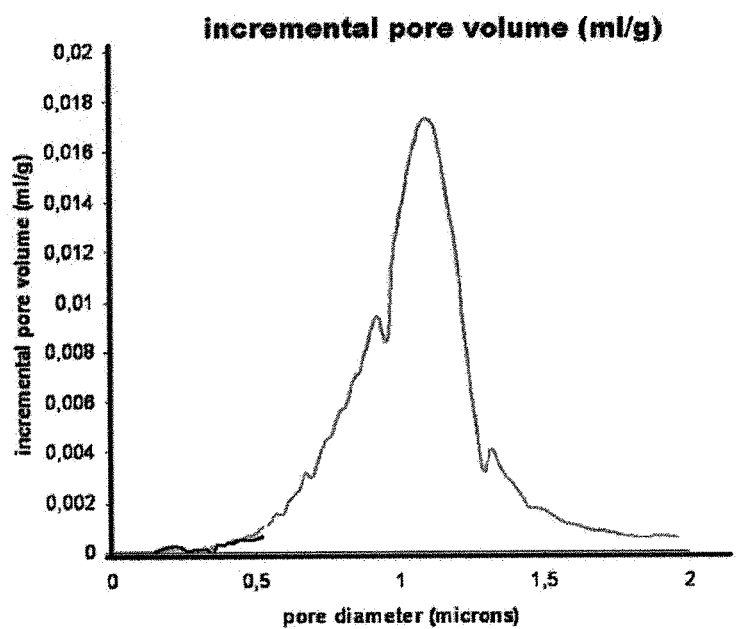

The results are presented in FIGS. 1-3, and show that the material prepared is chemically β-tricalcium phosphate containing a trace of Hydroxyapatite (FIG. 1). Interconnected micropores smaller than 2 μm distribute homogeneously in the material (FIG. 2), The size of the micropores is between 0.5-1.5 μm as measured with mercury intrusion (FIG. 3).

1.3 Animal Study and Histology

Figure 4:
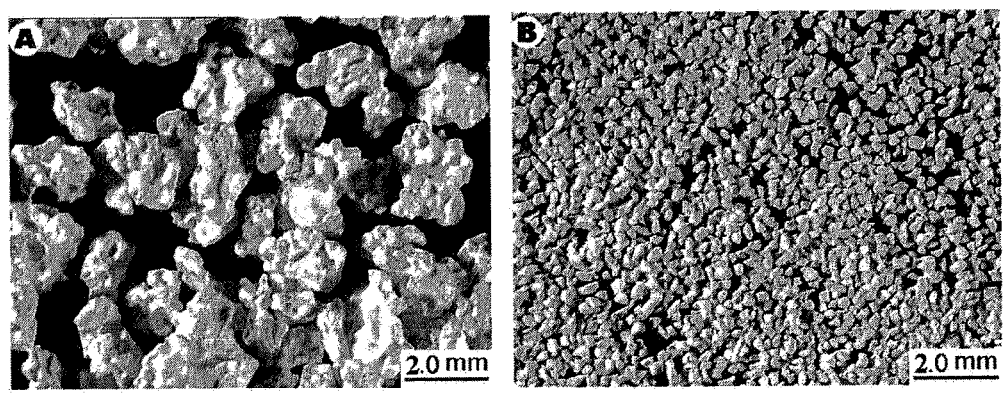
FIG. 4 shows the two implant materials used in Example 1: Microporous TCP particles having particle size 1-3 mm (panel A; comparative), and 212-300 µm (panel B; according to the present invention).

Implants consisted of a volume of 1.0 cc of ceramic particles. A control implant consisted of an implant with particle size of 1-3 mm (comparative example; FIG. 4A) and the test-implant consisted of an implant with particle size of 212-300 μm (material according to the present invention; FIG. 4B). Both types of implants were implanted in back muscles of dog. Eight dogs received both implants for 12 weeks. After 12 weeks, the implants were retrieved, including some surrounding tissues and were fixed in 10% buffered formation (pH=7.4). The fixed samples were dehydrated with series ethanol solutions (70%, 80%, 90%, 96% and 100%×2) and finally embedded in MMA. Non-decalcified sections (10-20 μm) were made and stained with methylene blue and basic fuchsin for histological observation and histomorphometrical analysis regarding formation. Histomorphometry was performed on the sections across the middle of the implants with regard to the percentage of the formed bone in the available space.

Figure 5:
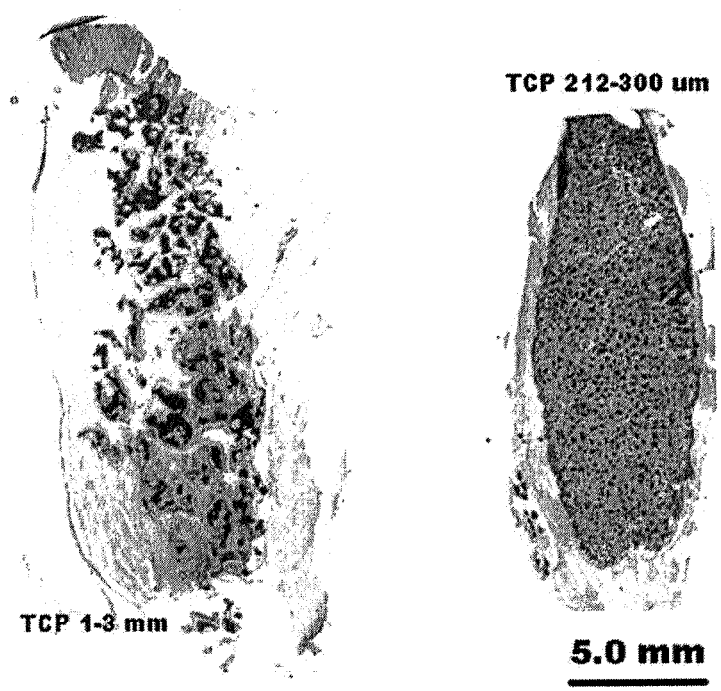
FIG. 5 represents micrographs of histological preparations of retrieved implants as described in Example 1. Bone formation (pink coloration) after 12-week implantation in muscle of dogs associated with an implant based on microporous particles of TCP having a particle size of 1-3 mm (left hand side) compared to the bone formation associated with an implant based on microporous particles of TCP having a particle size of 212-300 µm (right hand side).

The size or volume of the implants decreased (less than 1 cc) after intramuscular implantation in dogs for 12 weeks, indicating the resorbable nature of the TCP. Moreover, the remaining size of the implant of 1-3 mm particles is bigger than implant based on the particles with a size of 212-300 μm, indicating that the 212-300 μm microparticles are resorbed faster than 1-3 mm particles. Resorption of the materials was also observed histologically (FIG. 5). Intact TCP particles were visible in TCP implants based on the 1-3 mm particles, while most TCP microparticles (212-300 μm) broke down and resorbed.

Bone formation was seen in 6 out of 8 TCP implants of 212-300 μm microparticles and 8 out of 8 TCP implants of 1-3 mm. The most dramatic effect, however, was observed for the implant based on the 212-300 μm microparticles. Whereas bone formation associated with the particles of 1-3 mm was limited and confined to the particles themselves (FIG. 5, left hand side), massive and widespread bone formation was found to be associated with the microparticles of 212-300 μm and the bone was found to have formed primarily between the microparticles (FIG. 5, right hand side). Moreover, most of the microparticles were resorbed after 12-week implantation and the implants were actually transformed into a "real" autologous bone.

1.4 Discussion and Conclusion

The invention presents an enhanced inductive bone formation associated with implants having microporous calcium phosphates having micropores in size of 0.5-1.5 μm. Enhanced bone formation is observed by using this material in a particulate form and using specific particle size in the implants (i.e. microparticles, for instance 212-300 μm).

This approach now demonstrates to possibility of producing a real autologous bone in a non-osseous site and complete resorption of the calcium phosphate scaffold material.

Example 2 Material Properties Influencing Bone Forming Ability of the Two Tri-Calcium Phosphate Ceramics In this example, a comparison was performed between two tri-calcium phosphate ceramics having different grain size and micropore size, as well as different protein adsorption and bone forming abilities in an osteoinduction study model (non-osseous implantation).

2.1 the Materials

One TCP ceramic (TCP-01) was prepared according to methods of the present invention using $H_2O_2$ as a foaming agent method from an irregular shaped TCP powder with the size of 2.82 μm at D(v.0.5) (Table 1). Briefly the TCP powder was mixed with diluted $H_2O_2$ solution (0.1-5.0%; usually 2 wt %) and naphthalene particles (commercially purchased particles from Sigma-Aldrich are (optionally milled and) sieved through a sieve having mesh size 1400 μm, the fraction <1400 μm is used in this Example) to obtain a slurry of 100 g of TCP powder in 100-250 ml of $H_2O_2$ solution. After that, the slurry was foamed by placing the slurry in an oven without stirring at a temperature of 50-70° C., usually overnight. Then, the foamed slurry is dried in an oven at a temperature between 80-110° C. to obtain the porous green body. The porous green bodies were sintered at 1100° C. to get TCP-01. The sintered material was milled to provide ceramic particles, and a fraction of 1-3 mm was collected using sieves. The ceramic particles were then cleaned and sterilized for use. The other TCP (TCP-02) was Vitoss TCP, 1-4 mm, commercially available from Orthovita Inc., Malvern, Pa., USA, and was used as purchased.

TABLE 1

Particle size analysis of TCP powder for TCP-01*

| Size microns | % under | % in band | Size microns | % under | % in band | |
|---|---|---|---|---|---|---|
| 118 | 100 | 0.00 | 11.1 | 99.9 | 0.29 | Result source = Sample |
| 102 | 100 | 0.00 | 9.62 | 99.6 | 0.92 | Record No. = 0 |
| 88.1 | 100 | 0.00 | 8.30 | 98.7 | 2.03 | Focal length = 63 nm. |
| 76.0 | 100 | 0.00 | 7.16 | 96.7 | 3.35 | Presentation = oil |
| 65.6 | 100 | 0.00 | 6.18 | 93.3 | 4.88 | Volume distribution |
| 56.6 | 100 | 0.00 | 5.33 | 88.5 | 6.58 | Beam length = 2.0 nm. |
| 48.8 | 100 | 0.00 | 4.60 | 81.9 | 8.08 | Obscuration = 0.3803 |

TABLE 1-continued

Particle size analysis of TCP powder for TCP-01*

| Size microns | % under | % in band | Size microns | % under | % in band | |
|---|---|---|---|---|---|---|
| 42.1 | 100 | 0.00 | 3.97 | 73.8 | 9.28 | Volume Conc. = |
| 36.3 | 100 | 0.00 | 3.42 | 64.5 | 10.8 | 0.0039% |
| 31.3 | 100 | 0.00 | 2.95 | 53.7 | 11.9 | Log. Diff. = 3.180 |
| 27.0 | 100 | 0.00 | 2.55 | 41.8 | 10.6 | Model indp |
| 23.3 | 100 | 0.00 | 2.20 | 31.2 | 7.87 | D(v, 0.5) = 2.82 μm |
| 20.1 | 100 | 0.00 | 1.90 | 23.3 | 5.97 | D(v, 0.9) = 5.56 μm |
| 17.4 | 100 | 0.00 | 1.64 | 17.3 | 4.89 | D(v, 0.1) = 1.28 μm |
| 15.0 | 100 | 0.00 | 1.41 | 12.5 | 3.41 | D(4, 3) = 3.13 μm |
| 12.9 | 100 | 0.07 | 1.22 | 9.04 |  | D(3, 2) = 2.16 μm |
|  |  |  |  |  |  | Span = 1.52 |
|  |  |  |  |  |  | Spec. surf. area 2.7815 sq.m./cc. |

D(v.0.5) = 2.82 μm: in volume 50% of the particles are smaller than 2.82 μm.

2.2 Grain Sizes of TCP Ceramics

The grain sizes of TCP ceramics were measured in scanning electronic microscopic images at the magnification of 5000×. Using Adobe Photoshop® software, the biggest grains of the ceramics were marked and measured (FIG. 6). Ten grains were marked and measured for each TCP ceramic. The size of biggest grains in TCP-01 was 1.01±0.10 μm, while the size of the biggest grains in TCP-02 was 2.06±0.42 μm.

2.3 Micropore Size and Area Percentage of Micropores

The micropore size of TCP ceramics was measured in scanning electronic microscopic images at the magnification of 2500×. Using Adobe Photoshop® Elements software, micropores and TCP grains were selected with the magic wand tool and pseudocolored respectively (FIG. 7). To measure the micropore size, the pseudocolored images were printed and 10 biggest micropores were measured. To measure the area percentage of the micropores on the TCP surface, the area of interest was selected and the total number of pixels in the area of selection was counted. Then, the micropores were selected using the magic wand tool and the number of pixels associated with micropores was counted. Finally, the area percentage of micropores on the TCP surface was calculated as the number of pixels in a digital image associated with micropores as a percentage of the total number of pixels of the selected surface area. TCP-01 has micropores smaller than 0.95±0.28 μm and an area percentage of micropores of 22.4%, while TCP-02 has micropores smaller than 1.04±0.33 μm and area percentage of micropores of 4.4%.

2.4 Protein Adsorption

Figure 8:
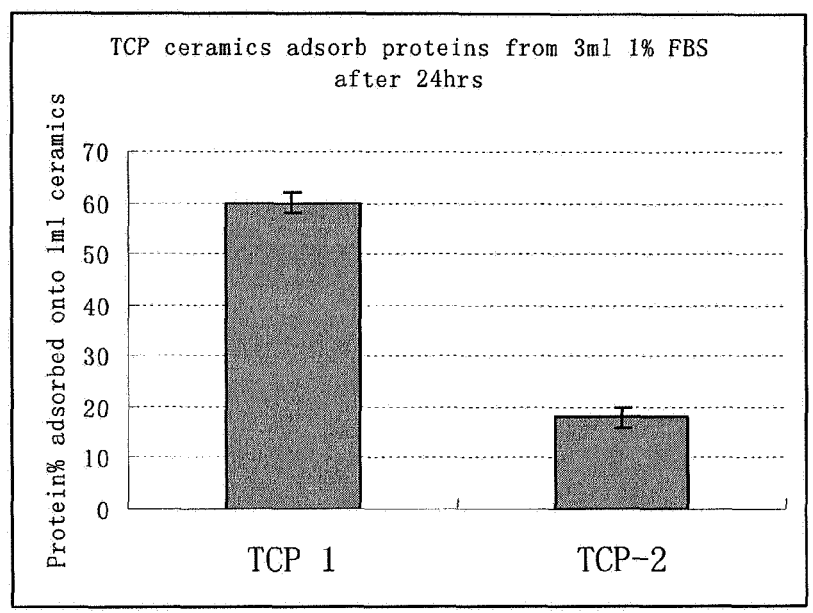
FIG. 8 shows the results in bar graphs of the protein adsorption of TCP ceramics from 1% FBS in 24 hrs as described in Example 2.

To test the protein adsorption, 1 ml of TCP ceramics were soaked in 3 ml of a 1% fetal bovine serum (FBS) solution in 25 ppm $NaN_3$. After incubating the samples at 37° C. for 24 hrs, protein assay was performed using a BCA™ Protein Assay Kit (Pierce Biotechnology Inc., Rockford, Ill., USA). In 24 hrs, TCP-01 was found to have adsorbed 60±3% of the proteins from the 3 ml of 1% FBS and TCP-02 adsorbed 18±2% (see FIG. 8).

2.5 Bone Forming Ability

Figure 9:
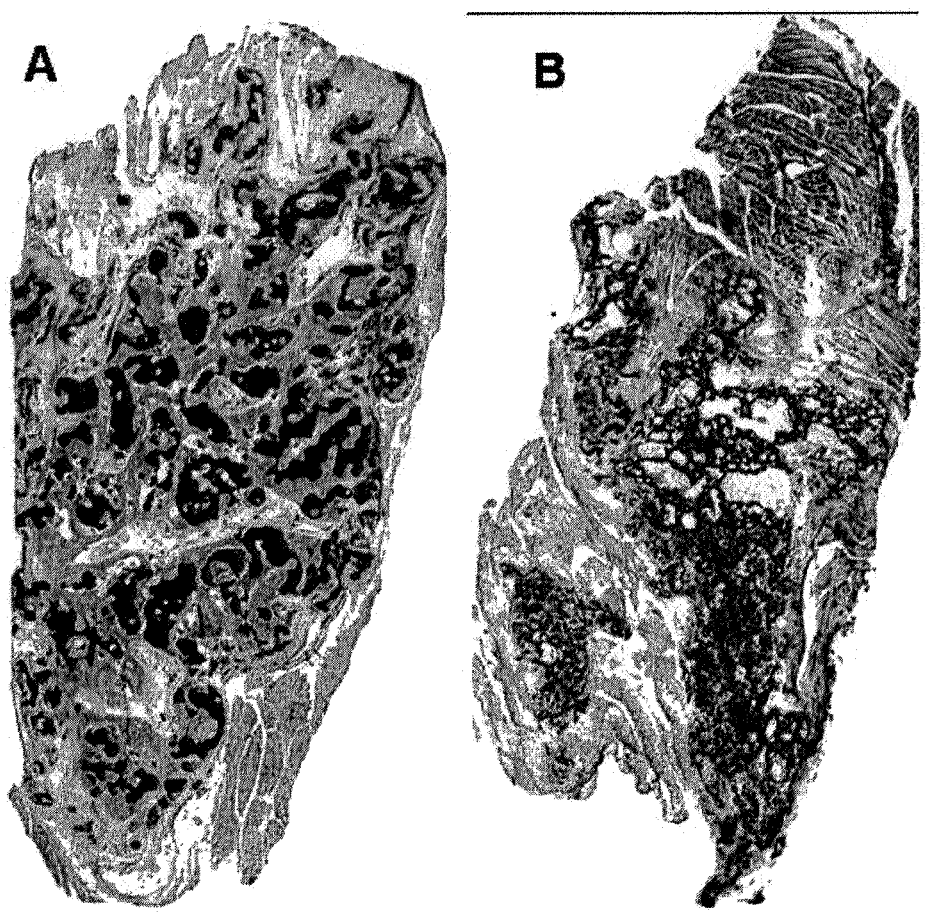
FIG. 9 shows histological micrographs of bone formation in TCP-01 (A) after 12-week implantation in muscle of dogs and no bone formation in TCP-02 (B) as described in Example 2.

To test the bone forming ability, 1 ml ceramic particles of TCP-01 and TCP-02 was implanted in back muscle of 8 dogs. Twelve weeks later, the animals were sacrificed and the samples were harvested with surrounding tissues. The samples harvested were then fixed with buffered formalin, dehydrated and embedded in MMA. Un-decalcified sections were made and stained with methylene blue and basic fuchsin for histological observation and histomorphometry. Abundant bone was formed in all TCP-01 implants (n=8) after a 12-week implantation in muscle of dogs and no bone was found in TCP-02 (FIG. 9). The area percentage of bone in TCP-01 was 15±9%.

2.6 Conclusion

Taking the grain size, micropore size, area percentage of micropores, protein adsorption and bone forming ability of the two tri-calcium phosphate ceramics into consideration, relations between grain size, micropore size, area percentage of micropores, protein adsorption and bone forming ability were found. Having a smaller grain size, a higher area percentage of micropores and a higher amount of protein adsorption, TCP-01 has a higher bone forming ability and is such an improved calcium phosphate ceramic. The improved calcium phosphate ceramics are thus defined as the calcium phosphate ceramics having grain size smaller than 1.50 μm (between 0.10-1.50 μm), micropore size smaller than 1.50 μm (between 0.10-1.50 μm), area percentage of micropores on calcium phosphate ceramic surface higher than 10% (between 10-40%) and higher protein adsorption which is equivalent to more than 40% protein (between 40-80%) from 3 ml 1% fetal bovine serum solution into 1.0 ml (or approximately 400 mg) porous ceramic particles (having total porosity of 80%) in 24 hrs.

Example 3 Effect of Calcium Phosphate Powder Type on Ceramic Properties

This example described the calcium phosphate powders for the improved calcium phosphate ceramics.

3.1 Calcium Phosphate Powders

Four TCP powders prepared with varied ways and having various shape and size were used in the example. They were power A, powder D, powder E and powder F. Powder A and E were oven dried milled while powder D and F were spray dried.

Figure 10:
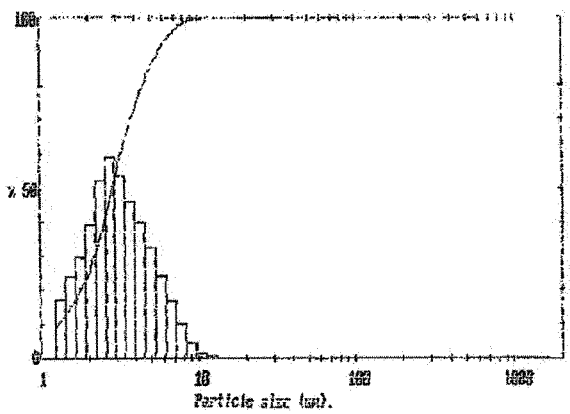
FIG. 10 illustrates the particle size distribution of powder E as described in Example 3.
Figure 11:
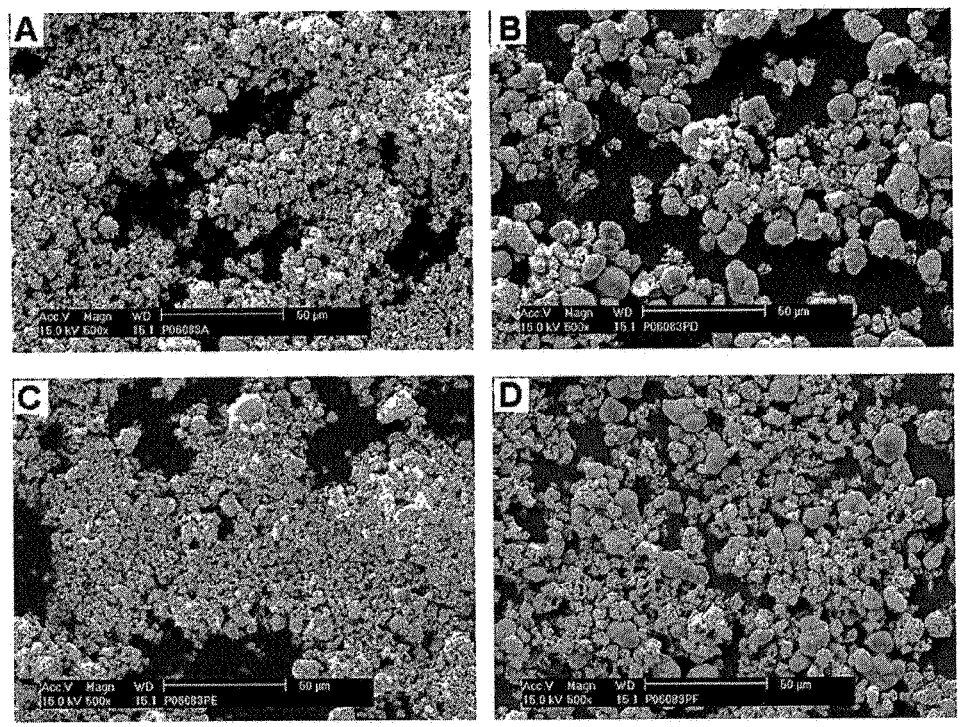
FIG. 11 shows the morphology of the 4 TCP powders under SEM observation (A, powder A; B: powder D; C: powder E and D: powder F) as described in Example 3.

All the 4 powders had a similar normal particle size distribution (FIG. 10) but different particles size. The particle size at D(v.0.5) for the various powders was: A, 2.79 μm; D, 11.60 μm; E, 2.82 μm, F, 7.80 μm. As compared under scanning electronic microscope, powder A and powder E had smaller irregular particles while powder D and powder F had larger and more spherical particles (FIG. 11).

3.2 Preparation of Calcium Phosphate Ceramics

TCP powders were mixed with diluted $H_2O_2$ solution (0.1-5.0%) and naphthalene particles (<1400 μm) to form slurries. The slurries were foamed at 40-70° C. and dried at 80-110° C. to provide green bodies. Thereafter the green bodies were sintered at 1100° C. for 8 hours. Finally ceramic particles (1-2 mm) were made, cleaned, dried and sterilized at 121° C. Four calcium phosphate ceramics were prepared respectively from 4 tri-calcium phosphate powders. They were ceramic A (from powder A), ceramic D (from powder D), ceramic E (from powder E) and ceramic F (from powder F).

3.3 Grain Size

Figure 12:
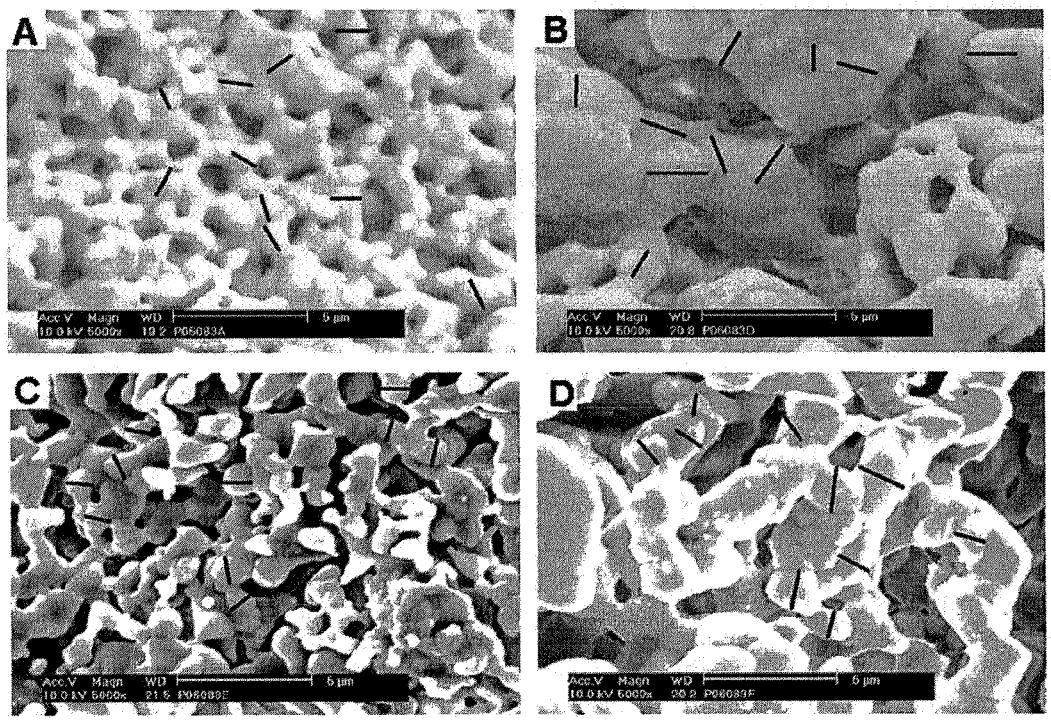
FIG. 12 shows the grains in the various ceramics (A, ceramic A; B ceramic D; C, ceramic E and D, ceramic F) as described in Example 3.

The grain sizes of the 4 TCP ceramics were measured in scanning electronic microscopic images at the magnification of 5000×. Using Adobe Photoshop® software, the biggest grains of the ceramics were marked and printed (FIG. 12). Ten grains were marked and measured for each TCP ceramic. The size of biggest grains was 1.14±0.12 μm in ceramic A, 1.56±0.36 μm in ceramic D, 1.01±0.10 μm in ceramic E and 1.30±0.31 μm for ceramic F.

3.4 Micropore Size and Area Percentage of Micropores

Figure 13:
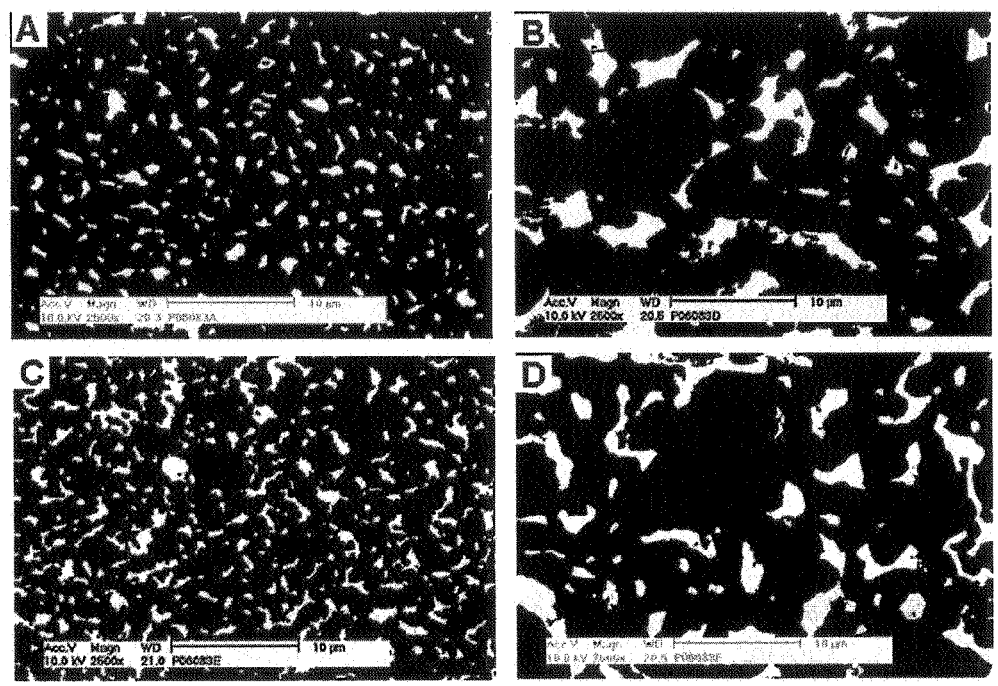
FIG. 13 shows the micropores on the surface of the various ceramics (A, ceramic A; B ceramic D; C, ceramic E and D, ceramic F) (black: TCP grains; white: micropores) as described in Example 3.

The micropore size of TCP ceramics was measured in scanning electronic microscopic images at the magnification of 2500×. Using Adobe Photoshop® Elements software, micropores and TCP grains were selected with magic wand tool and pseudocolored respectively (FIG. 13). To measure the micropore size, the pseudocolored images were printed and 10 biggest micropores were measured. To measure the area percentage of the micropores on TCP surface, the area of interest was selected and the pixels were counted read, then the micropores were selected with magic wand tool and the pixels were counted. Finally, the area percentage of micropores on TCP surface was calculated as described in Example 2. The micropore size and area percentage of micropores on ceramic surface were respectively 0.73±0.12 μm and 10.1% for ceramic A, 1.23±0.33 μm and 14.5% for ceramic D, 0.0.95±0.28 μm and 22.4% for ceramic E, 1.23±0.21 μm and 16.1% for ceramic F.

3.5 Protein Adsorption

Figure 14:
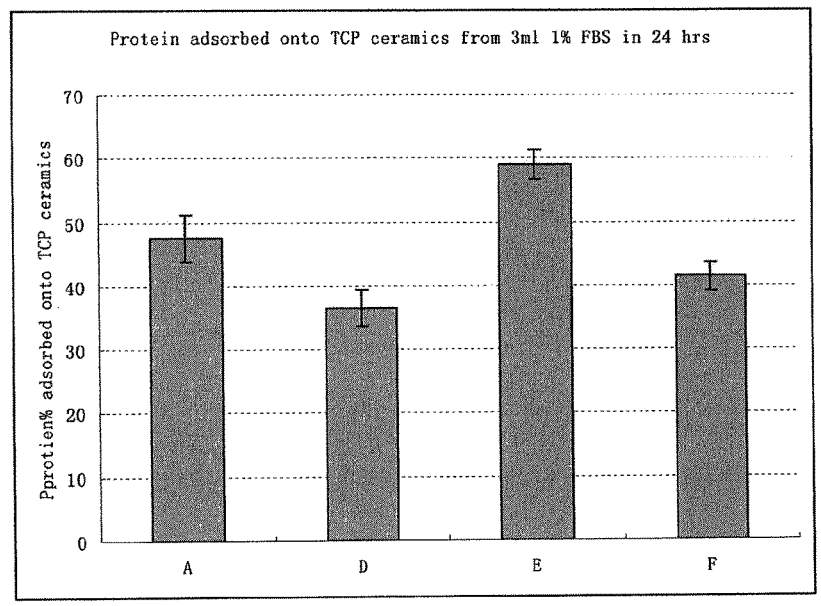
FIG. 14 shows the protein adsorption of the various ceramics from 1% FBS in 24 hrs, as described in Example 3.

To test the protein adsorption, 1 ml of TCP ceramics were soaked in 3 ml 1% FBS in 25 ppm $NaN_3$.solution. After incubating the samples at 37° C. for 24 hrs, protein assay was performed with BCA kit. In 24 hrs, ceramic A adsorbed 48±4% protein from 3 ml 1% fetal bovine serum (FBS) solution, ceramic D adsorbed 36±3%, ceramic E adsorbed 59±2% and ceramic F adsorbed 41±2% (FIG. 14).

3.6 Conclusion

Ceramics prepared from 4 TCP powders had varied characteristics, due to either the ways in which the powders were produced and/or the particle size and/or particle size distributions. Table 2 showed that ceramics prepared from powder A [oven dried milled, irregular particles with powder particle size of 2.79 μm at D(v.0.5)], powder E [oven dried milled, irregular particles with powder particle size of 2.82 μm at D(v.0.5)] and powder F [spray dried, spherical particles with powder particle size of 7.80 μm at D(v.0.5)] had very similar characteristics over the range of parameters tested and showed in particular improved protein absorption in combination with small grain size. Ceramic D, on the other hand, prepared from powder D [spray dried, spherical particles with powder particle size of 11.60 μm at D(v.0.5)] showed reduced protein absortion capacity in combination with grain size >1.5 μm. It is therefore concluded that, oven dried milled powders with irregular shapes and having a powder particle size of 2.00-4.00 μm at D(v.0.5) are preferred for producing the improved calcium phosphate ceramics, spray dried powders having spherical particles larger than 8.0 μm are less suitable.

TABLE 2

Characterizations of ceramics prepared from different powders

|  | Required for improved ceramic | Ceramic A | Ceramic D | Ceramic E | Ceramic F |
|---|---|---|---|---|---|
| Grain size | <1.50 μm | 1.14 μm | 1.56 μm | 1.01 μm | 1.30 μm |
| Micropore size | <1.50 μm | 0.73 μm | 1.23 μm | 0.95 μm | 1.23 μm |
| Area % of micropores | >10% (10-40%) | 10.1% | 14.5% | 22.4% | 16.1% |
| Protein adsorption | >40% (40-80%) | 48% | 36% | 59% | 41% |
| Improved ceramic? |  | yes | No | yes | yes |

Example 4 Method for Preparing a Calcium Phosphate Ceramic Having Improved Osteoinductive Properties This example describes the manufacture of calcium phosphate ceramics using a method of the present invention with $H_2O_2$ as a foaming agent as compared to a method using Isostatic Pressing.

4.1 the Calcium Phosphate Powders

The calcium phosphate powder used in this example was spray dried tri-calcium phosphate (TCP) powder having spherical particles with size of 7.80 μm at D(v.0.5)

4.2 the Ceramics

Two ceramics particles were made, herein referred to as TCP-$H_2O_2$ and TCP-press.

TCP-$H_2O_2$ was prepared using $H_2O_2$ as a foaming agent. Briefly, TCP powder was mixed with diluted $H_2O_2$ solution (0.1-5.0%) and naphthalene particles (<1400 μm) to form a slurrie, then the slurries were foamed at 40-70° C. and dried at 80-110° C. to obtain green bodies. Thereafter the green bodies were sintered at 1100° C. for 8 hours. Finally, ceramic microparticles (212-300 μm) were made by milling, and particles were cleaned and dried.

TCP-press was prepared with Isostatic Pressing. TCP powder was mixed with water, and pressed firstly at 1 MPa for 1 minute then at 5 MPa for 5 minutes. The obtained material (in the form of cylinders) was dried at 60° C. and then sintered at 1100° C. Finally ceramic microparticles (212-300 μm) were made by milling, and particles were cleaned and dried.

4.3 Grain Size

Figure 15:
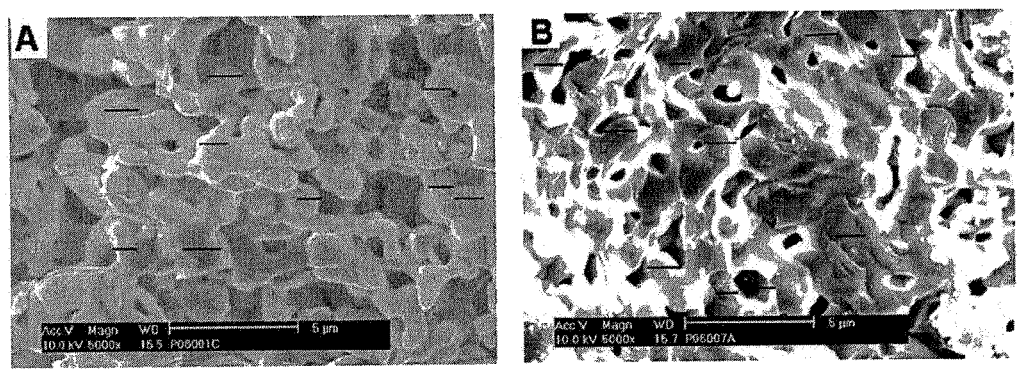
FIG. 15 shows the grains in TCP ceramics (A, TCP-$H_2O_2$ and B: TCP-press) as described in Example 4.

The grain size of the 2 TCP ceramics was measured using scanning electronic microscopic images at a magnification of 5000×. Using Adobe Photoshop® software, the biggest grains of the ceramics were marked and measured (see FIG. 15). Ten grains were marked and measured for each TCP ceramic. The size of biggest grains was 1.15±0.21 μm in TCP-$H_2O_2$ and 1.07±0.20 μm in TCP-press.

4.4 Micropore Size and Area Percentage of Micropores

Figure 16:
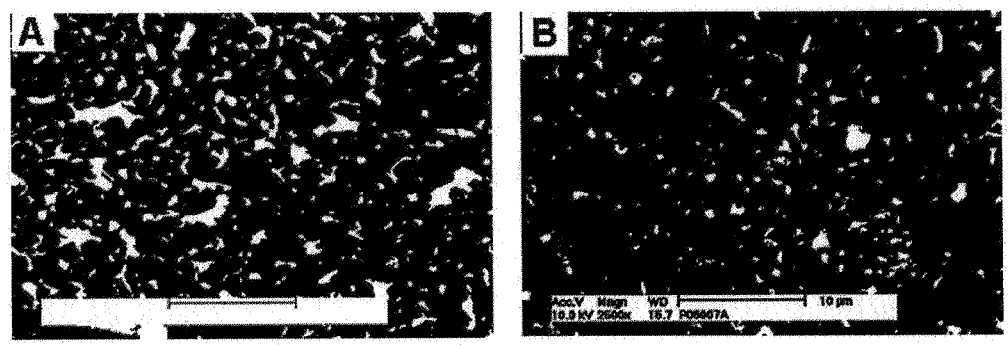
FIG. 16 indicates the micropores on the ceramic surfaces (A, TCP-H$_2$O$_2$ and B: TCP-press) (black: TCP grains; white: micropores) as described in Example 4.

The micropore size of the two TCP ceramics was measured using scanning electronic microscopic images at the magnification of 2500×. Using Adobe Photoshop® Elements® software, micropores and TCP grains were selected using the "magic wand" tool and filled using pseudocolours respectively (see FIG. 16). To measure the micropore size, the pseudocolored images were printed and 5 of the biggest micropores were measured. To measure the area percentage of the micropores on TCP surface, the area of interest was selected and the pixels were counted, then the micropores were selected using the "magic wand" tool and the pixels marked thereby were counted. From these two countings, the area percentage of micropores per TCP surface was calculated as described above. The micropore size and area percentage of micropores on ceramic surface were respectively 1.28±0.10 μm and 14.1% for TCP-$H_2O_2$, 1.06±0.45 μm and 5.4% for TCP-press

4.5 Protein Adsorption

Figure 17:
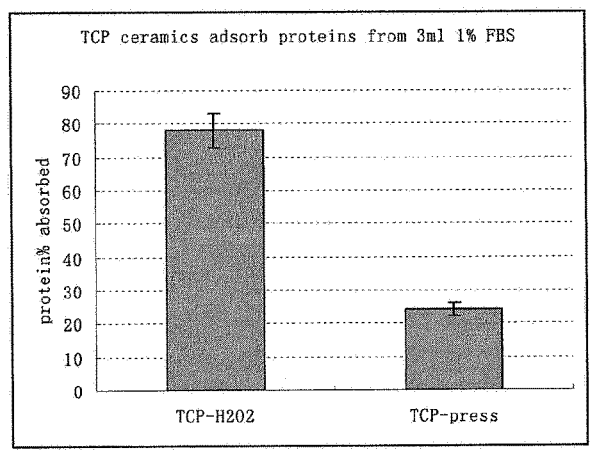
FIG. 17 shows the protein adsorption of ceramics from 1% FBS in 24 hrs as described in Example 4.

To test the protein adsorption, 1 ml of TCP ceramics were soaked in 3 ml 1% FBS in 25 ppm $NaN_3$ solution. After incubating the samples at 37° C. for 24 hrs, protein assay was performed with BCA kit. In 24 hrs, TCP-$H_2O_2$ adsorbed 78±5% protein from 3 ml 1% fetal bovine serum (FBS) solution, TCP-press adsorbed 24±2% (FIG. 17).

4.6 Conclusion

Ceramics prepared with $H_2O_2$ method and Isostatic Pressing had varied characteristics. Table 3 showed that TCP-$H_2O_2$ exhibited a higher area percentage of micropores and had better protein absorption characteristics than TCP-press. It is therefore concluded that, $H_2O_2$ method is preferred over the Isostatic Pressing method in improving the osteoinductive properties of calcium phosphate ceramics.

TABLE 3

Characterizations of ceramics prepared with $H_2O_2$ and Isostatic Pressing

| | Required for improved ceramic | TCP-H2O2 | TCP-press |
|---|---|---|---|
| Grain size | <1.50 μm | 1.15 μm | 1.07 μm |
| Micropore size | <1.50 μm | 1.28 μm | 1.06 μm |
| Area % of micropores | >10% (10-40%) | 14.1% | 5.4% |
| Protein adsorption | >40% (40-80%) | 78% | 24% |
| Improved ceramic? | | yes | No |

Example 5 Effect of Sintering Temperature on Calcium Phosphate Ceramics

This example illustrates the effect of sintering temperature in a method for preparing a calcium phosphate ceramic on the osteoinductive properties of the calcium phosphate ceramic thus prepared.

5.1 the Calcium Phosphate Powder

The calcium phosphate powder used in this example was oven dried milled TCP powder having irregular particles with size of 2.11 μm at D(v.0.5)

5.2 the Ceramics

Ceramics were prepared with $H_2O_2$ method but sintered at different temperatures of 1050° C., 1075° C. and 1100° C. Briefly, TCP powder was mixed with diluted $H_2O_2$ solution (0.1-5.0%) and naphthalene particles (<1400 μm) to form slurries, then the slurries were foamed at 40-70° C. and dried at 80-110° C. to get porous green bodies. Thereafter the green bodies were sintered at 1050° C., 1075° C. and 1100° C. respectively for 8 hours. Finally ceramic particles (1-2 mm) were made, cleaned, dried and sterilized at 121° C.

5.3 Grain Size

Figure 18:
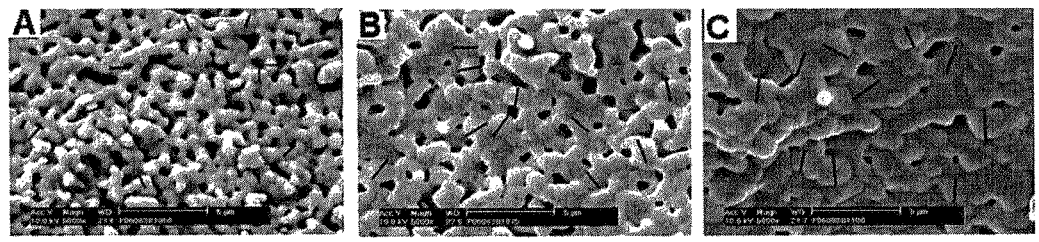
FIG. 18 shows the grains in TCP ceramics sintered at different temperatures (A, 1050° C.; B, 1075° C. and C, 1100° C.) as described in Example 5.

The grain sizes of the 3 TCP ceramics were measured in scanning electronic microscopic images at the magnification of 5000×. Using Adobe Photoshop® software, the biggest grains of the ceramics were marked and printed (FIG. 18). Ten grains were marked and measured for each TCP ceramic. The size of biggest grains was 0.76-±0.08 μm in TCP sintered at 1050° C., 1.30±0.12 μm in TCP sintered at 1075° C. and 1.53±0.20 μm in TCP sintered at 1100° C.

5.4 Micropore Size and Area Percentage of Micropores

Figure 19:
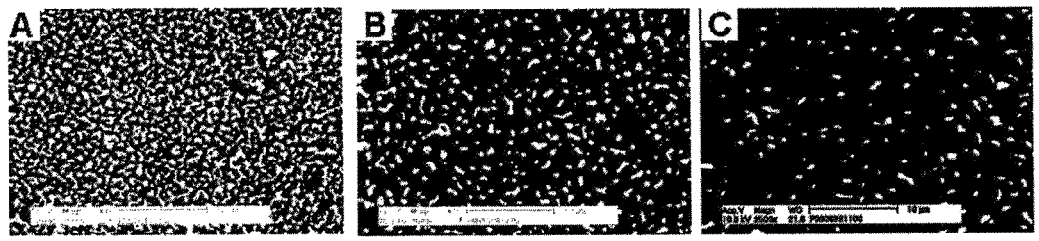
FIG. 19 shows the micropores on the surface of the various ceramics sintered at different temperatures (A, 1050° C.; B1075° C. and C: 1100° C.) (black: TCP grains; white: micropores) as described in Example 5.

The micropore size of TCP ceramics were measured in scanning electronic microscopic images at the magnification of 2500×. Using Adobe Photoshop® Elements software, micropores and TCP grains were selected with magic wand tool and pseudocolored respectively (FIG. 19). To measure the micropore size, the pseudocolored images were printed and 10 biggest micropores were measured.

To measure the area percentage of the micropores on TCP surface, the area of interest was selected and the pixels was read, then the micropores were selected with magic wand tool and the pixels were read. At the end the area percentage of micropores on TCP surface was calculated. The micropore size and area percentage of micropores on ceramic surface were respectively 0.58±0.0.09 μm and 24.2% for TCP sintered at 1050° C., 0.62±0.12 μm and 11.3% for TCP sintered at 1075° C., 0.47±0.19 μm and 4.5% for TCP sintered at 1100° C.

5.5 Protein Adsorption

Figure 20:
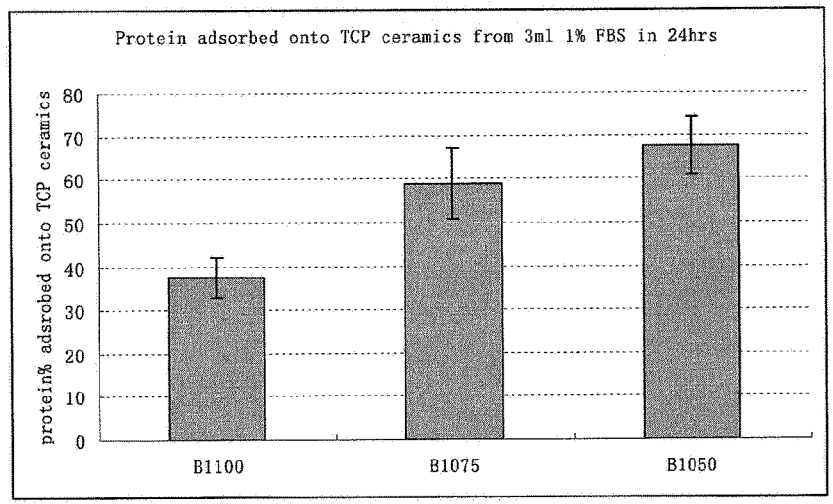
FIG. 20 shows the protein adsorption of the ceramics from 1% FBS in 24 hrs (B1050, TCP 1050° C.; B1057, TCP1075° C. and B1100, TCP 1100° C.) as described in Example 5.

To test the protein adsorption, 1 ml of TCP ceramics were soaked in 3 ml 1% FBS in 25 ppm $NaN_3$ solution. After incubating the samples at 37° C. for 24 hrs, protein assay was performed with BCA kit. In 24 hrs, TCP sintered at 1050° C. adsorbed 68±7% protein from 3 ml 1% fetal bovine serum (FBS) solution, TCP sintered at 1075° C. adsorbed 59±8% protein, and TCP sintered at 1100° C. adsorbed 37±5% protein (FIG. 20).

5.6 Conclusion

Ceramics sintered at different temperatures had varied characteristics. Table 4 showed that TCP sintered at 1100° C. exhibited larger grain size and lower protein absorption capacity that calcium phosphate ceramic sintered at 1050° C. or 1075° C. It is therefore concluded that, to improve osteoinductive properties of tri-calcium phosphate ceramics, the sintering temperature should preferable not exceed 1100° C., preferably around 1050-1075° C.

TABLE 4

Characterizations of ceramics sintered at different temperature.

|  | Required for improved ceramic | TCP sintered at 1050° C. | TCP sintered at 1075° C. | TCP sintered at 1100° C. |
|---|---|---|---|---|
| Grain size | <1.50 µm | 0.76 µm | 1.30 µm | 1.53 µm |
| Micropore size | <1.50 µm | 0.58 µm | 0.62 µm | 0.47 µm |
| Area % of micropores | >10% (10-40%) | 24.2% | 11.3% | 4.5% |
| Protein adsorption | >40% (40-80%) | 68% | 59% | 37% |
| Improved ceramic? |  | yes | yes | No |

The invention claimed is:

1. A porous osteoinductive calcium phosphate material having an average grain size in a range of 0.1-1.50 µm, a porosity comprising micropores in a size range of 0.1-1.50 µm and being free of macropores and having a surface area percentage of micropores in a range of 10-40% over a surface of the porous osteoinductive calcium phosphate material, the porous osteoinductive calcium phosphate material being osteoinductive in a non-osseous site, wherein the porous osteoinductive calcium phosphate material has a protein adsorption capacity, expressed as a percentage of protein absorbed by a volume of 1 ml of said calcium phosphate material from a volume of 3 ml of a 1% aqueous solution of fetal bovine serum (FBS) in the presence of 25 ppm sodium azide ($NaN_3$) after 24 hrs at 37° C., of at least 40%.

2. The porous osteoinductive calcium phosphate material according to claim 1, wherein the porous osteoinductive calcium phosphate material is in the form of microparticles having a particle size ranging from about 50 µm to about 1500 µm.

3. The porous osteoinductive calcium phosphate material according to claim 2, wherein the microparticles have a particle size ranging from about 200 µm to about 300 µm.

4. The porous osteoinductive calcium phosphate material according to claim 2, wherein the microparticles have a particle size ranging from about 212 µm to 300 µm.

5. The porous osteoinductive calcium phosphate material according to claim 1, wherein the calcium phosphate is chosen from the group consisting of octacalcium phosphate, apatites, whitlockites, and combinations thereof.

6. The porous osteoinductive calcium phosphate material according to claim 1, wherein the calcium phosphate is resorbable biphasic calcium phosphate (BCP) or resorbable tricalcium phosphate.

7. The porous osteoinductive calcium phosphate material according to claim 1 for use as a medical implant material or tissue scaffold.

8. The porous osteoinductive calcium phosphate material according to claim 1, wherein the porosity consists essentially only of micropores in the size range of 0.1-1.50 µm.

9. The porous osteoinductive calcium phosphate material according to claim 1, wherein the non-osseous site comprises living tissues.

10. The porous osteoinductive calcium phosphate material according to claim 1, wherein the porous osteoinductive calcium phosphate material is applied as a coating to another material.

11. The porous osteoinductive calcium phosphate material according to claim 1, wherein the porosity is interconnected.

* * * * *